(12) United States Patent
Vanaclocha Vanaclocha

(10) Patent No.: US 8,480,743 B2
(45) Date of Patent: Jul. 9, 2013

(54) UNIVERSAL DISC PROSTHESIS

(76) Inventor: Vicente Vanaclocha Vanaclocha, Valencia (ES)

(*) Notice: Subject to any disclaimer, the term of this patent is extended or adjusted under 35 U.S.C. 154(b) by 0 days.

(21) Appl. No.: 13/064,444

(22) Filed: Mar. 25, 2011

(65) Prior Publication Data

US 2012/0245688 A1     Sep. 27, 2012

(51) Int. Cl.
*A61F 2/44* (2006.01)

(52) U.S. Cl.
USPC ............. 623/17.15; 623/17.14; 623/17.16

(58) Field of Classification Search
USPC .......... 623/17.11–17.16, 19.12, 20.14, 20.21, 623/20.22, 20.24, 20.26, 21.13, 21.16, 23.4; 606/246; 403/113–115, 125, 126
See application file for complete search history.

(56) References Cited

U.S. PATENT DOCUMENTS

| | | | | |
|---|---|---|---|---|
| 6,770,095 B2* | 8/2004 | Grinberg et al. | ........... | 623/17.14 |
| 8,057,547 B2* | 11/2011 | Hurlbert et al. | ........... | 623/17.14 |
| 8,246,685 B2* | 8/2012 | Sournac et al. | ........... | 623/17.16 |
| 8,277,509 B2* | 10/2012 | Hansell et al. | ........... | 623/17.16 |
| 8,343,222 B2* | 1/2013 | Cope | ........... | 623/17.14 |
| 8,366,772 B2* | 2/2013 | Ferree et al. | ........... | 623/17.11 |
| 2006/0235526 A1* | 10/2006 | Lemaire | ........... | 623/17.14 |
| 2008/0228274 A1* | 9/2008 | De Villiers et al. | ........... | 623/17.14 |
| 2009/0048680 A1* | 2/2009 | Naegerl | ........... | 623/20.14 |
| 2011/0160862 A1* | 6/2011 | De Villiers et al. | ........... | 623/17.16 |
| 2013/0006371 A1* | 1/2013 | Wogoman et al. | ........... | 623/20.21 |

* cited by examiner

*Primary Examiner* — Michael T Schaper

(57) ABSTRACT

A disc prosthesis designed to effectively replace a damaged intervertebral disc, enabling the various normal movements between two adjacent vertebral bodies and controlling these movements and their extent within the same physiological limits that determine the relative motions of two adjacent vertebrae separated by a healthy intervertebral disc.

2 Claims, 10 Drawing Sheets

SECTION A-A

SECTION B-B

UNIVERSAL DISC PROSTHESIS

OBJECT OF THE INVENTION

The object of the present invention is a disc prosthesis designed to effectively replace a damaged intervertebral disc, enabling the various normal movements between two adjacent vertebral bodies and controlling these movements and their extent within the same physiological limits that determine the relative motions of two adjacent vertebrae separated by a healthy intervertebral disc.

BACKGROUND OF THE INVENTION

There are in the art various types of disc prosthesis designed to enable one or more of the movements of flexion-extension, lateral bending and rotation between two adjacent vertebrae.

All of them have the drawback that they facilitate movement within excessive limits. Indeed, constructive solutions for disc prosthesis aim to ensure that movements, mainly flexion and extension, lateral bending and rotation, can be easily and smoothly made but at the same time they do not avoid the significant problems that can occur when anyone of these movements exceeds the physiological limits of the spine of each person.

Therefore, although getting a patient to regain normal range of motion of the spine is a major achievement, it is a potential danger that flexion-extension, lateral flexion or rotation exceed limits which may seriously impair the structures adjacent to the vertebral bodies causing, for example, degeneration of the facet joints, or may even affect the integrity of the spinal cord or, more commonly, that of the nerve roots that come out of it.

Therefore, there is a need to provide a disc prosthesis that avoids the drawbacks mentioned above by ensuring that the movements provided by the prosthesis have essentially the same limits as the patient's physiological limits.

One such disc prosthesis is claimed in appended claim 1.

BRIEF SUMMARY OF THE INVENTION

The universal disc prosthesis of the invention is a device designed to replace an intervertebral disc located between any two adjacent vertebrae in the spine, the device consisting of two parts: an upper part adapted to join in a conventional manner to the upper vertebra of the two adjacent vertebrae, and a lower part adapted to join in a conventional manner to the lower vertebra of the two adjacent vertebrae. The way of permanently attaching each part to its corresponding vertebra can be any of those known in the art. In normal operation, the two parts are not linked by any connecting element.

The shape and dimensions of the surfaces of the two parts of the prosthesis of the invention that will be in fixed contact with the vertebral bodies are substantially equal to the corresponding surfaces of the vertebral bodies. The shapes and dimensions can be varied to make the prosthesis of the invention can be manufactured with shapes and dimensions suitable for installation in different regions of the spine, so that the universal disc prosthesis of the invention is suitable to fit the intervertebral spaces of either the cervical spine, or the thoracic spine, or the lumbar spine. In practice, the prosthesis is particularly useful for the lower cervical vertebrae and for the lumbar vertebrae, because the thoracic spine has limited mobility; the inventor is not aware of any disc prosthesis being ever implanted at the thoracic spine.

The upper and lower parts of the prosthesis of the invention are each provided with a surface of interface for contact and operative interaction between the two parts. Both surfaces of interface are essentially complementary in that, for example, a concave area in the upper part matches a corresponding convex area in the lower part, but they are not exactly complementary, so that when the prosthesis has been implanted and both surfaces of interface are brought to proper relative positions, several relative motions between said upper and lower part with certain limitations in scope and range may take place.

These limitations to the relative movements must conform to the physiological limits imposed by the configuration of the spinal vertebrae. For the purposes of the invention, and bearing in mind that the physiological characteristics of the column are different for different individuals, the limits listed in Table 1 will be taken as indicative:

TABLE 1

| Spine area | Flexion extension movement | Lateral bending movement | Rotation |
| --- | --- | --- | --- |
| Cervical | 5-10° | 6° | 7° |
| Thoracic | 4° | 2° | 2° |
| Lumbar | 11° | 5° | 1° |

The disc prosthesis of the invention has features that allow the prosthesis to adapt, by varying their overall shape and dimensions, intervertebral spaces of each of the three spine areas mentioned above providing the necessary range of motion within the limits for each area indicated in Table 1.

The novelty of the invention lies essentially in the relationship between forms and aspect ratios of the interfaces of both upper and lower parts and in the relative position between them.

The lower part has an interface whose surface comprises a first base plane from which a partial area of the interface is essentially projecting (hereinafter and for simplicity, "lower projection") and the upper part has an interface whose surface comprises a second base plane relative to which a partial area of the interface is essentially a recess (hereinafter and for simplicity, "upper recess").

The shape features of the two parts are described below. It should be understood that the general characteristics of shape of the lower part are generally complementary to those of the upper part, in that convex or flat areas of the lower part have a descriptive correspondence with concave or flat areas of the upper part. However, the aspect ratios are different for each part, and complementary areas of each part show different aspect ratios, these differences and proportions defining the scope and control of the limitations of relative movements between the lower and upper parts.

For the purposes of identifying features of the prosthesis of the invention, and in a conventional coordinate system used for both the lower projection and the upper recess, "X" is defined as the longitudinal axis of each part of the prosthesis, "Y" as the transverse axis (axis which, once the prosthesis is positioned in a spine, would be located in the sagittal plane), said axes "X" and "Y" being located at the base plane, and "Z" as the axis perpendicular to the base plane. Consequently, XZ plane is defined as a longitudinal plane through each part of the prosthesis, and YZ plane is defined as a transverse plane through each part of the prosthesis. Where the terms "lower" or "upper" are used to define the position of parts of the prosthesis, it should be understood as referring to the position of those parts on a prosthesis when said parts are placed in the same relative positions as when placed on a spine of a patient.

The lower projection, as well the upper recess, is symmetric about the XZ and YZ planes and the shape of its surface is generally convex (concave in the case of the upper recess). Different areas of the surface have different spherical or cylindrical curvature radii so that the relative motion of the lower projection relative to the upper recess provided of surface areas with corresponding radii of curvature can take place smoothly and gradually.

An important feature of the prosthesis of the invention that makes a difference relative to the prior art is that the lower projection, and correspondingly the upper recess, are provided of a zone of discontinuity on the surface generally convex (respectively, concave in case of the upper recess). This zone of discontinuity is located in a central area of the projection (respectively recess) in the direction of the longitudinal axis included in the XZ plane. Said zone of discontinuity in the lower projection is characterized in that it comprises two cavities symmetric about the longitudinal plane XZ as well as about the transverse plane YZ, in the upper recess, correspondingly, the zone of discontinuity is characterized by comprising two convexities symmetric about the longitudinal plane XZ as well as about the transverse plane YZ.

While the remaining features of the lower projection and of the upper recess are intended to facilitate and smooth the relative movements between the two parts, said zones of discontinuity are intended to limit those movements on an appropriate and gradual way. To this end, shapes of both lower projection and upper recess are substantially complementary, but their respective characteristics of shape and dimensions are defined to maintain proportions, these proportions resulting in some restrictions on movements between the upper and lower part of the prosthesis of the invention. These limits vary depending on the location in the column where the prosthesis of the invention should be placed.

BRIEF DESCRIPTION OF THE SEVERAL VIEWS OF THE DRAWINGS

The invention will now be described by means of two preferred embodiments with reference to the accompanying drawings, in which:

FIG. 1b is a plan view of the lower part of FIG. 1a;

FIG. 1c is a side elevational view of the lower part of FIG. 1a;

FIG. 1d is a transversal cross-section of the lower part of FIG. 1a;

FIG. 2b is a longitudinal cross-section of the upper part of FIG. 2a;

FIG. 2c is a transversal cross-section of the upper part of FIG. 2a;

FIG. 3b is an elevational view of the lower part of FIG. 3a;

FIG. 3c is a side elevational view of the lower part of FIG. 3a;

FIG. 4b is a longitudinal cross-section of the upper part of FIG. 4a.

DETAILED DESCRIPTION OF PREFERRED EMBODIMENTS OF THE INVENTION

Figure 1A:
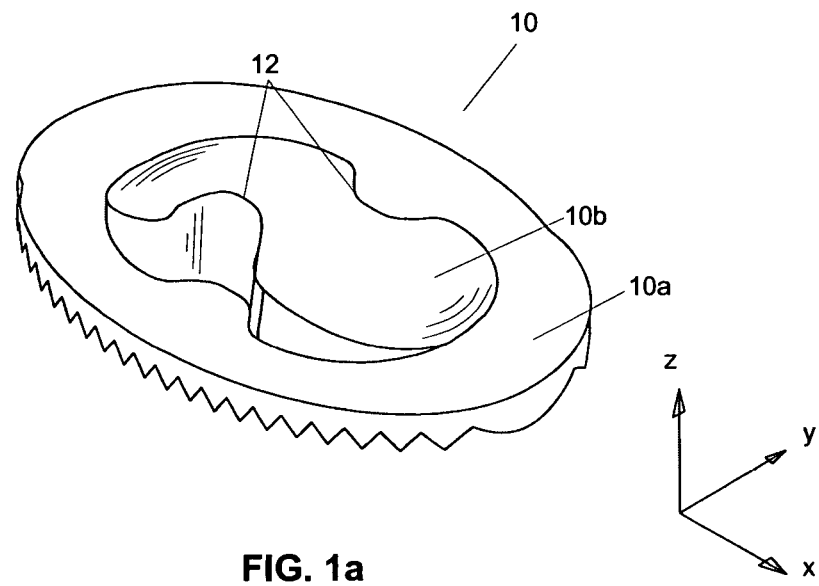
FIG. 1a is a schematic perspective view of a lower part of a first preferred embodiment of the prosthesis of the invention which is suitable for a lumbar spine.
Figure 1B:
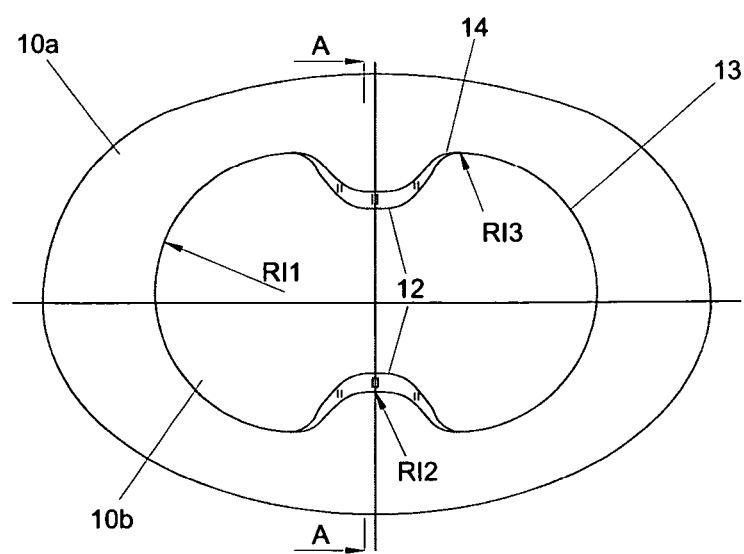
Figure 1C:
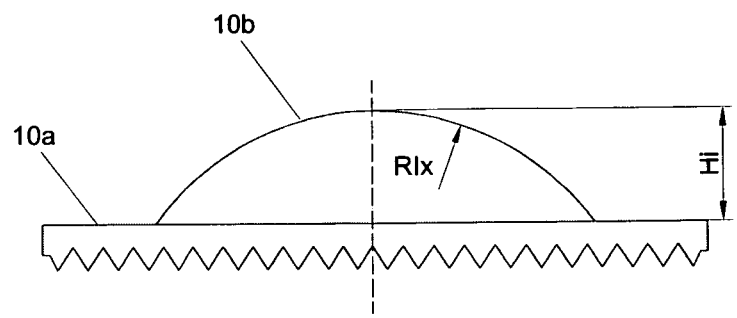
Figure 1D:
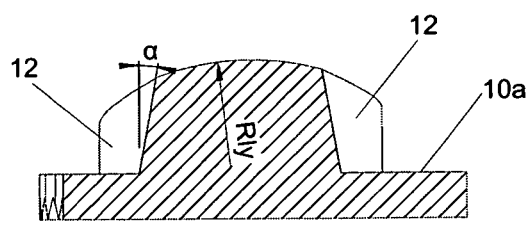

FIGS. 1a-1d and 2a-2c show a first preferred embodiment of the prosthesis of the invention particularly suitable for thoracic and lumbar areas. FIGS. 1a-1d show a lower part 10 of the prosthesis comprising a bottom surface adapted to be secured to a lower vertebra and an upper surface which is a first interface surface for contact and interaction between said lower part 10 and a second interface surface in the upper part 20 of the prosthesis of the invention, said first interface surface comprising a first base plane 10a and a projection 10b generally convex (hereinafter, lower projection) projecting from said first base plane 10a; referring to the lower projection 10b of the lower part 10, a first central zone of discontinuity 11 is characterized by having two cavities 12 symmetrically located on either side of the longitudinal plane of symmetry XZ of said lower projection 10b.

Therefore, the cavities 12 are symmetric to each other about the plane XZ, and the two cavities share a common plane of symmetry YZ. These cavities 12 have a wall surface substantially conical with an angle $\alpha$ of inclination about an axis perpendicular to the XY plane corresponding to a cone angle of $2\alpha$, the cone having a vertex located in a lower position. However, the ends of the wall surface in the longitudinal direction (X axis), ie further away from the plane of symmetry YZ, have an inclination angle $\alpha'$, being $\alpha'$ substantially less than $\alpha$.

The axis of revolution of the conical surface of said cavities 12 is perpendicular to the first base plane 10a of the first interface surface and the length of the circular arc Ai with radius $RI_2$, which is the line of intersection between said tapered surface and the first base plane 10a of the first surface interface, shows a ratio equal to or less than ⅔ relative to the length of the circle arc of the intersection between the first base plane 10a and each of the end convex zones of lower projection 10b outside of the first central zone of discontinuity 11.

A longitudinal cross-section of the lower projection 10b by the XZ plane is shaped like a circular segment of radius $RI_x$. A cross section of the lower projection 10b by the YZ plane is shaped like a trapezium with a circular top side with a radius $RI_y$, the sloping sides of the trapezium defining the maximum depth along the Y axis of the two, symmetric cavities 12 made in the lower projection 10b. The ratio $RI_x/RI_y$ may vary from 1.25 to 1.50.

The periphery of the lower projection 10b has at its intersection with the first base plane 10a, and in the longitudinal direction (X-axis direction), two convex ends 13 in the form of circular arcs of less than 180 degrees and radius $RI_1$, connected by two central concave circle arcs of 60 to 80 degrees and radius $RI_2$ belonging to the cavities 12. The aspect ratio of the radius $RI_1$ of the convex end 13 and the radius $RI_2$ of the central concave circle arcs belonging to the cavities 12 is from 0.70 to 0.80. The four transitional areas between the arc of the convex ends 13 to the concave circle arcs of radius $RI_2$ are small convex arcs 14 of less than 45 degrees and radius $RI_3$, being 0.2 to 0.3 the ratio $RI_3/RI_2$.

Figure 2A:
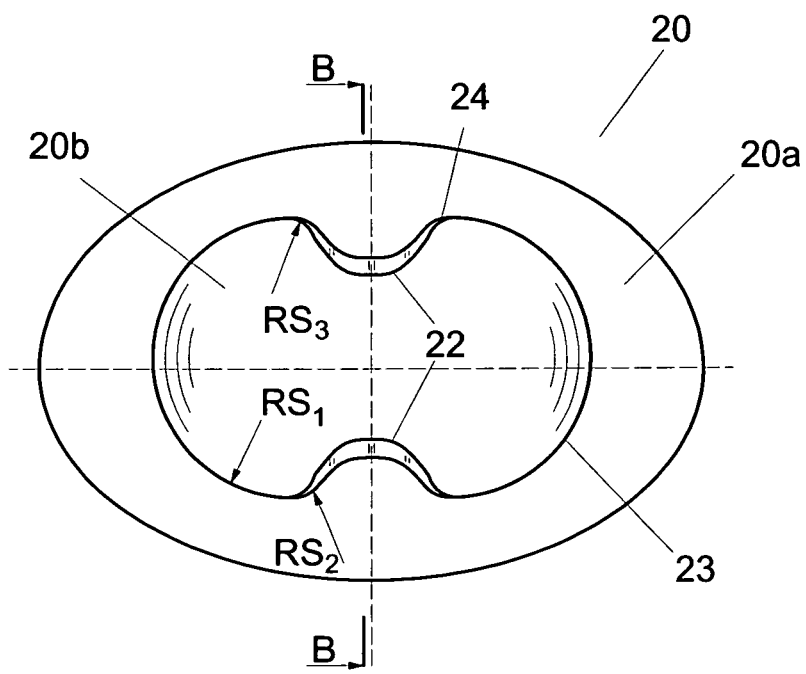
FIG. 2a is a plan view of an upper part of the first preferred embodiment of the prosthesis of the invention.
Figure 2B:
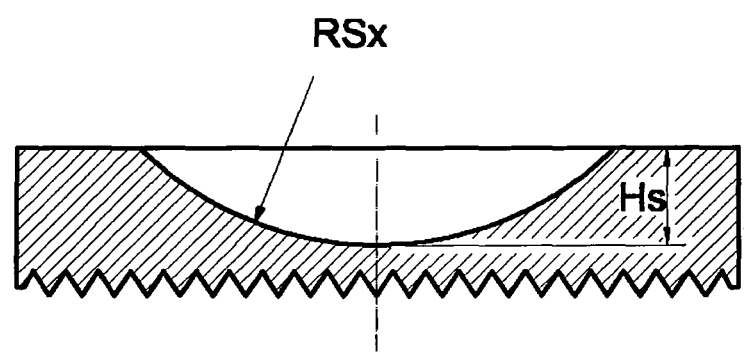
Figure 2C:
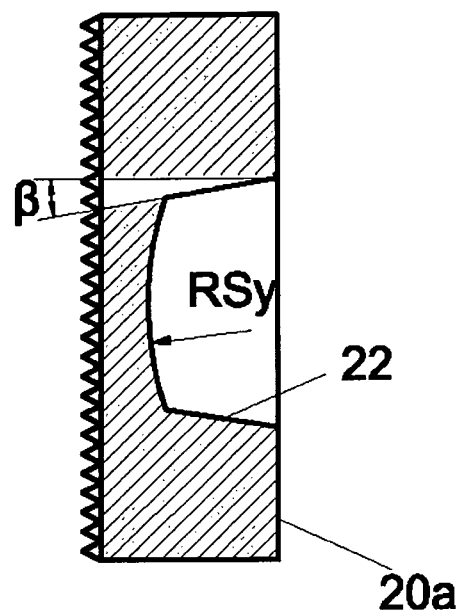

FIGS. 2a-2c show the upper part 20 of the prosthesis comprising an upper surface adapted to be secured to an upper vertebra and a lower surface which is a second interface surface for contact and interaction between said upper part 20 and the second interface surface in the lower part 10 of the prosthesis of the invention, said second interface surface comprising a second base plane 20a and a recess 20b (hereinafter, upper recess) generally concave incoming from said second base plane 20a, in reference to the upper recess 20b of the upper part 20, a second central zone of discontinuity 21 is characterized by having two convexities 22 symmetrically located on either side of the longitudinal plane of symmetry XZ of said upper recess 20b. Correspondingly with the features of lower projection, the convexities 22 are symmetric to each other about the plane XZ, and the two convexities share the common plane of symmetry YZ. These convexities 22 have a substantially conical wall with an angle β of inclination about an axis perpendicular to the XY plane corresponding to a cone angle equal to 2β, the cone having a vertex located in a lower position. However, the ends of the wall surface in the longitudinal direction (X axis), ie further away from the plane of symmetry YZ, have an inclination angle β', being β' substantially less than β. The angles β, β' in the upper recess 20b are respectively lower than the angles of inclination α, α' on the lower projection 10b.

The axis of revolution of the conical surface of said convexities 22 is perpendicular to; the second base plane 20a of the second interface surface and the length of the circular arc $A_s$ with radius $RS_2$, which is the line of intersection between said tapered surface and the second base plane 20a of the second surface interface is proportionate value equal to or less than ⅔ relative to the length of the circle arc of the intersection between the second base plane 20a and each of the end concave zones of upper recess 20b outside of the second central zone of discontinuity 21.

A longitudinal cross-section of the upper recess 21 by the XZ plane is shaped like a circular segment with radius $RS_x$. A cross section of the upper recess 21 by the YZ plane is shaped like a trapezium with a circular lower base with radius $RS_y$; the sloping sides of the trapezium defining the maximum heights along the Y axis of the two symmetric convexities 22 made in the upper recess 20b. The ratio $RS_x/RS_y$ may vary between 1.25 and 1.50.

The periphery of the upper recess 20b has at its intersection with the second base plane 20a, and in the longitudinal direction (X-axis direction), two concave ends 23 in the form of circular arcs of less than 180 degrees and radius $RS_1$, connected by two central convex circle arcs of 60 to 80 degrees and radius $RS_2$, belonging to the convexities 22. The aspect ratio of the $RS_1$ of the concave end 23 and the radius $RS_2$ of the central convex circle arcs belonging to the convexities 22 is from 0.70 to 0.80. The four transitional areas between the arcs of concave ends 23 to the convex circle arcs of radius $RS_2$ are small concave arcs 24 of less than 45 degrees and radius $RS_3$, being 0.2 to 0.3 the ratio $RS_3/RS_2$.

The ratio between the radii $RI_2$ of the central concave areas of the lower projection 10b and the radio $RS_2$ of the central convex areas of upper recess 20b, is 1.25-1.35.

When the second interface surface of the upper part 20 and the first interface surface of the lower part 10 are coupled together in operating position, the extent of relative rotation between upper recess 20b and lower projection 10b which takes place in YZ plane is limited due to the different inclinations of angle β of the walls of symmetric convexities 22 in the upper part 20 and the angle α of the walls of the symmetric cavities 12 of the lower part 10. The larger this difference, the greater the extent of relative rotation between upper recess 20b and lower projection 10b in a plane YZ. The limits to that movement appear when the walls of the convexities 22 and cavities 12 come into contact. When the prosthesis of the invention is in operation, the limits to said relative rotation are equal to or lower than the physiological limits shown in Table 1 for the movement of flexion extension.

Similarly, when the second interface surface of the upper part 20 and the first interface surface of the lower part 10 are coupled together in an operating position, the extent of relative rotation between upper recess 20b and lower projection 10b which takes place in XZ plane is limited due to the different inclinations of angle β' of the ends of the walls of the symmetric convexities 22 of the upper part 20 and angle α' of the ends of the walls of the symmetric cavities 12 of the lower part 10. The larger this difference, the greater the extent of relative rotation between upper recess 20b and lower projection 10b in a plane XZ. The limits to that movement appear when the walls of the convexities 22 and cavities 12 come into contact. When the prosthesis of the invention is in operation, the limits to said relative rotation are equal to or lower than the physiological limits shown in Table 1 for the movement of lateral bending.

In regard to the relative rotation of the upper part 20 with respect to the lower part 10 which may take place in an XY plane when the second interface surface of the upper part 20 and the first interface surface of the lower part 10 are coupled together in operating position, the extent of relative rotation between upper recess 20b and lower projection 10b which takes place in XY plane is limited due to the clearance between the substantially conical walls of each cavity 12 of lower projection 10b and the corresponding convexity 22 of upper recess 20b. The higher the clearance, the greater the extent of relative rotation between upper recess 20b and lower projection 10b in a plane XY. The limits to that movement appear when the walls of the convexities 22 and cavities 12 come into contact. When the prosthesis of the invention is in operation, the limits to said relative rotation are equal to or lower than the physiological limits shown in Table 1 for the movement of rotation.

To allow relative movement between the upper part 20 and lower part 10, the height Hi of the lower projection 10b above the first base plane 10a is greater than the depth Hs of the upper recess 20b below the second base plane 20a. The difference (Hs−Hi) must exceed a minimum amount to prevent an unwanted contact between the first plane base 10a and the second base plane 20a in the movements of flexion-extension and lateral bending.

The aspect ratios listed in Table 2 have proven to be particularly suitable for prostheses of the invention to be placed in the thoracic and lumbar spine. Table 2 shows proportions that determine the limitations of the different movements of the prosthesis of the invention in accordance with the physiological limits shown in Table 1.

TABLE 2

| Movement | Suitable ratio |
| --- | --- |
| Flexo extension | $RS_y/RI_y = 1.25$-$1.50$ |
|  | $(H_s - H_i) > 2$ mm |
|  | $20° < α < 35°$ |
|  | $α/β = 1.45$-$1.75$ |
| Lateral bending | $RS_x/RI_x = 1.25$-$1.50$ |
|  | $(H_s - H_i) > 2$ mm |
|  | $20° < α < 35°$ |
|  | $α'/β' = 1.33$-$1.50$ |
| Rotation | $A_I/A_s = 1.10$-$1.15$ |
|  | $RS_1/RI_1 = 1.10$-$1.25$ |
|  | $RI_2/RS_2 = 1.25$-$1.35$ |

Figure 3A:
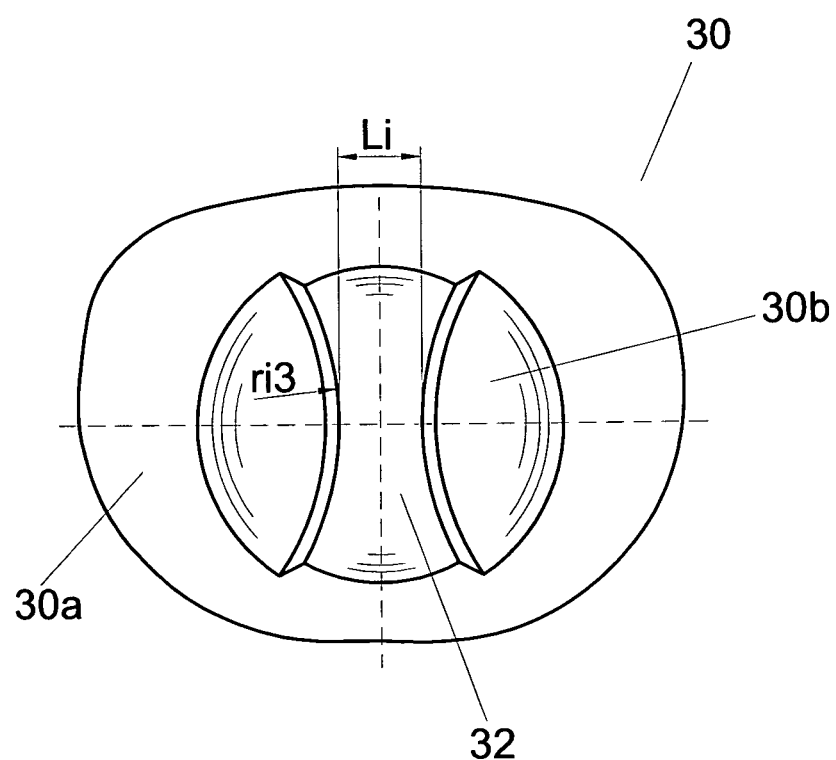
FIG. 3a is a plan view of a lower part of a second preferred embodiment of the prosthesis of the invention which is suitable for a cervical spine.
Figure 3B:
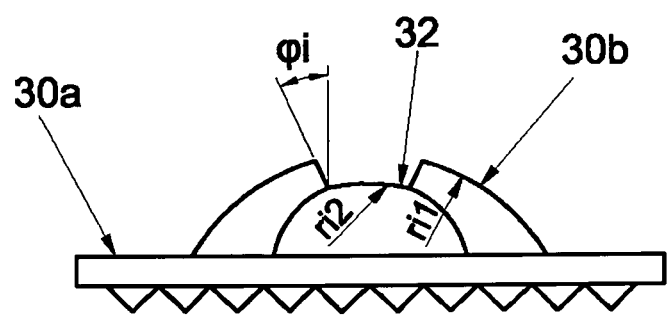
Figure 3C:
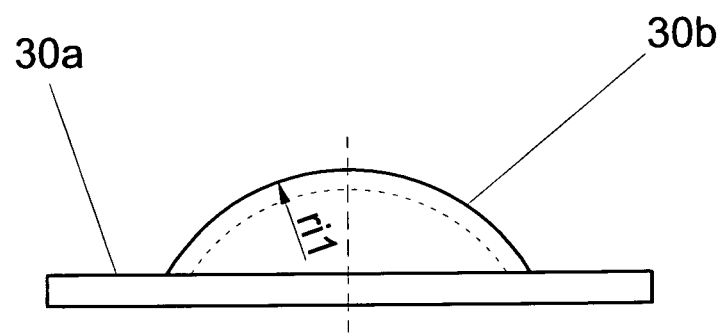

FIGS. 3a-3c and 4a-4b show a second preferred embodiment of the prosthesis of the invention, more particularly suitable for the cervical area. FIGS. 3a-3c show a lower part 30 of the prosthesis comprising a bottom surface adapted to be secured to a lower vertebra and an upper surface which is a third interface surface for contact and interaction between said lower part 30 and a fourth interface surface in an upper part 40 of the prosthesis, said third interface surface comprising a third base plane 30a and a projection 30b generally convex spherical with radius ri$_1$ (hereinafter, lower projection) projecting from said third base plane 30a; referring to the lower projection 30b of the lower part 30, a third central zone of discontinuity 31 is characterized by having a continuous cavity or recess 32 in the generally convex spherical surface of the lower projection 30b.

The purpose of said continuous cavity or recess 32 is the same as that pursued in the first preferred embodiment by the two symmetric cavities 12 made in the lower projection 10b, and the fact that the recess 32 is continuous is due to the convenience in practice of linking these two cavities continuously in the prosthesis of the invention suitable for the cervical spine, which should have a substantially smaller size than the prosthesis of the invention suitable for thoracic and lumbar spine.

The continuous recess 32 is of uniform depth so that its bottom is a generally spherical surface with radius r$_{i2}$, which is concentric with the generally spherical surface with radius r$_{i1}$ of the lower projection 30b. The shape of the continuous recess 32 is symmetric about the XZ and XY planes. The periphery of the continuous recess 32 is formed by two circular symmetric and opposed arcs with radius r$_{i3}$, whose minimum separation Li occurs in the intersection of lower projection 30b by the plane XZ. The transition from the generally spherical surface (outer surface) of lower projection 30b to the generally spherical shape of the bottom of continuous recess 32 is provided by a wall that is not perpendicular to both said spherical surfaces at each point of the periphery of the continuous recess 32 but instead it shows a constant angle of inclination $\phi_i$ with each of said spherical surfaces at each point on the periphery of the continuous recess 32.

Figure 4A:
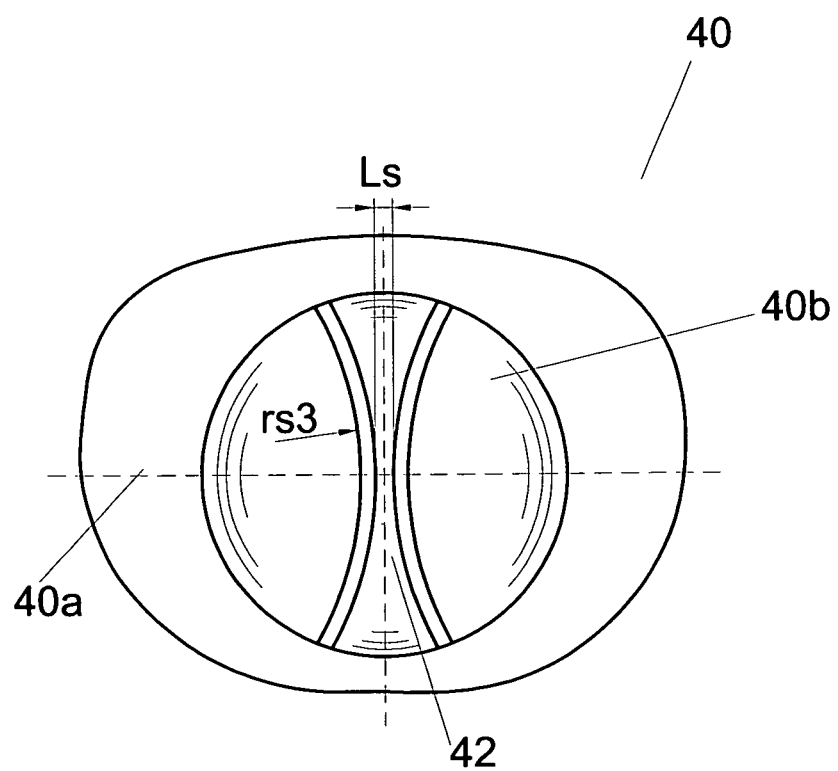
FIG. 4a is a plan view of an upper part of the second preferred embodiment of the prosthesis of the invention.
Figure 4B:
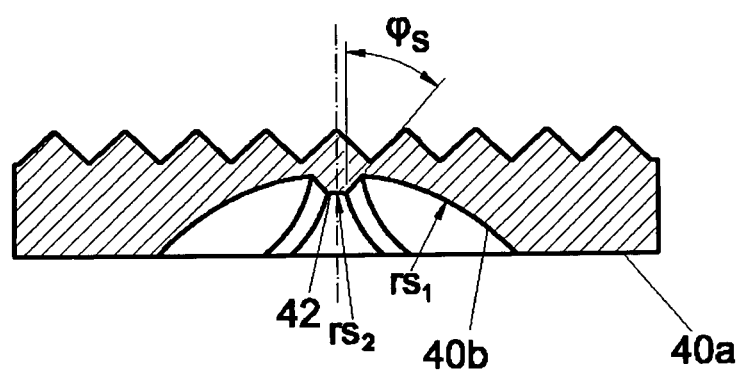

Correspondingly, FIGS. 4a-4b show the upper part 40 of the prosthesis comprising an upper surface adapted to be secured to an upper vertebra and a lower surface which is a fourth interface surface for contact and interaction between said upper part 40 and the third interface surface in the lower part 30 of the prosthesis of the invention, said fourth interface surface comprising a fourth base plane 40a and a recess 40b generally convex spherical with radius rs$_1$ (hereinafter, upper recess) incoming from said fourth base plane 30a; referring to the upper recess 40b of the upper part 40, a fourth central zone of discontinuity 41 is characterized by having a continuous shoulder 42 on the generally concave spherical surface of the upper recess 40b. The shoulder 42 is of uniform height and its most salient part is preferably a spherical surface with radius r$_{s2}$ which is concentric with the generally spherical surface with radius rs$_1$ of the upper recess 40b. The shoulder 42 is symmetric about the XZ and XY planes. The periphery of the shoulder 42 is formed by two symmetric opposed arcs with radius r$_{s3}$, whose minimum separation Ls occurs in the intersection of the upper recess 40b by the XZ plane, Ls being higher than the minimum separation Li in the lower projection 30b.

The transition from the generally spherical surface (inner surface) of the upper recess 40b to the generally spherical surface with radius r$_{s2}$ of the most salient area of shoulder 42 is provided by a wall that is not perpendicular to both said spherical surfaces at each point on the periphery of shoulder 42 but instead it shows a constant angle of inclination $\phi_s$ with each of said spherical surfaces at each point on the periphery of the shoulder 42. Said angle $\phi_s$ is lower than $\phi_i$ and keep a constant ratio with it.

To allow relative movement between the upper 40 and lower part 30, the height Hi of the lower projection 30b above the third base plane 30a is greater than the depth Hs of the upper recess 40b below the fourth base plane 40a. The difference (Hs−Hi) must exceed a minimum amount to prevent an unwanted contact between the third plane base 30a and the fourth plane base 40a of the fourth upper recess interface 40b in the movements of flexion-extension and lateral bending The aspect ratios listed in Table 3 have proven to be particularly suitable for prostheses of the invention to be placed in the cervical spine. Table 3 shows proportions that determine the limitations of the different movements of the prosthesis of the invention in accordance with the physiological limits shown in Table 1.

TABLE 3

| Movement | Suitable ratio |
| --- | --- |
| Flexo extension and Lateral bending | $r_{s1}/r_{s2}$ = 1.10-1.20 |
|  | $r_{i2}/r_{i1}$ = 1.10-1.20 |
|  | $L_s/L_i$ = 1.15-1.25 |
|  | $r_{s1}/r_{i1}$ = 1.25-1.50 |
|  | 15° < $\phi_i$ < 25° |
|  | $\phi_s/\phi_i$ = 0.75-0.90 |
| Rotation | $r_{s3}/r_{i3}$ = 1.05-1.10 |
|  | $L_s/L_i$ = 1.15-1.25 |
|  | $\phi_s/\phi_i$ = 0.75-0.90 |

The prosthesis of the invention is capable of being locked, when clinically advisable, to eliminate any relative movements between the two parts that compose it. For that purpose, it is only necessary to make two threaded holes located in a plane parallel to the interface base planes and passing through the upper part and the lower projection in the lower part, and then introduce screws into those threaded holes.

Having described the prosthesis of the invention, as well as two preferred embodiments thereof, it is only necessary to add that there may be changes in configuration and dimensions without departing from the essence of the invention claimed below.

The invention claimed is:

1. A disc prosthesis comprising:
   a lower part comprising a lower surface adapted to be secured to a lower vertebra and an upper surface which is a first interface surface, said first interface surface comprising a first base plane, and a convex projection which is a lower projection projecting from said first base plane, and
   an upper part comprising an upper surface adapted to be secured to an upper vertebra and a lower surface which is a second interface surface, said second interface surface comprising a second base plane, and a concave recess which is an upper recess incoming from said second base plane;
   wherein
   said first and second interface surfaces are generally complementary because concave regions of the first interface surface operatively match with convex regions of the second interface surface and convex regions of the first interface surface operatively match with concave regions of the second interface surface for contact and operating interaction between said first and second interface surfaces;
   wherein
   said lower projection of the lower part has a shape symmetric about a longitudinal plane and about a transverse plane, and comprises a first central zone of discontinuity characterized by having two cavities which are symmetric to each other about said longitudinal plane and also share a common plane of symmetry which is said transverse plane of symmetry of said lower projection;

the two cavities each have a wall surface substantially conical with an angle α of inclination about an axis perpendicular to the first base plane, said angle α corresponding to an angle of 2α of a cone having a vertex located in a lower position, with the exception of two end zones of said wall surface further away from the transverse plane of symmetry which show an inclination angle α', being α' less than α;

a longitudinal cross-section of the lower projection by said longitudinal plane is shaped like a circular segment of radius $RI_x$, a cross section of the lower projection by said transverse plane of symmetry is shaped like a trapezium with a circular top side with a radius $RI_y$, sloping sides of the trapezium defining maximum depths along a transverse direction of said two cavities;

a periphery of the lower projection has at its intersection with said first base plane, and in a longitudinal direction, two convex ends in the form of circle arcs of less than 180 degrees and radius $RI_1$, connected by four transitional areas to two central concave circle arcs of 60 to 80 degrees and radius $RI_2$ belonging to said two cavities, said four transitional areas between said convex ends and said concave circle arcs being small convex circle arcs of radius $RI_3$;

wherein said upper recess of said upper part has a shape symmetric about a longitudinal plane and about a transverse plane, and comprises a second central zone of discontinuity characterized by having two convexities which are symmetric to each other about said longitudinal plane and also share a common plane of symmetry which is said transverse plane of symmetry of said upper recess;

said two convexities each have a wall surface substantially conical with an angle β of inclination about an axis perpendicular to the second base plane, said angle β corresponding to an angle of 2β of a cone having a vertex located in a lower position, with the exception of two end zones of said wall surface further away from said transverse plane of symmetry of said upper recess which show an inclination angle β', being β' less than β;

a longitudinal cross-section of the upper recess by said longitudinal plane of the upper recess is shaped like a circular segment of radius $RS_x$, a cross-section of the upper recess by said transverse plane of symmetry of the upper recess is shaped like a second trapezium with a circular lower side with radius $RS_y$, sloping sides of the second trapezium defining maximum heights along a transverse direction of said two symmetric convexities;

the periphery of the upper recess has at its intersection with said second base plane, and in a longitudinal direction, two concave ends in the form of circle arcs of less than 180 degrees and radius $RS_1$, connected by four transitional areas to two central convex circle arcs of 60 to 80 degrees and radius $RS_2$ belonging to said two convexities, said four transitional areas between said concave ends and said convex circle arcs being small convex circle arcs of radius $RS_3$;

and wherein ratio $RS_Y/RI_Y$ is from 1.25 to 1.50;
ratio $RS_X/RI_X$ is from 1.25 to 1.50;
ratio α/β is from 1.45 to 1.75
ratio α'/β' is from 1.33 to 1.50
ratio $RS_1/RI_1$ is from 1.10 to 1.25, and
ratio $RI_2/RS_2$ is from 1.25 to 1.35, so that the disc prosthesis is suitable for a lumbar spine of a patient.

2. A disc prosthesis comprising:

a lower part comprising a lower surface adapted to be secured to a lower vertebra and an upper surface which is a third interface surface, said third interface surface comprising a third base plane, and a convex spherical projection having a spherical surface with radius $ri_1$ which is a lower projection projecting from said third base plane, and an upper part comprising an upper surface adapted to be secured to an upper vertebra and a lower surface which is a fourth interface surface, said fourth interface surface comprising a fourth base plane and a concave spherical recess having a spherical surface with radius $rs_1$ which is an upper recess incoming from said fourth base plane;

wherein said third and fourth interface surfaces are generally complementary because concave regions of the third interface surface operatively match with convex regions of the fourth interface surface and convex regions of the third interface surface operatively match with concave regions of the fourth interface surface for contact and operating interaction between said third and fourth interface surfaces;

wherein said lower projection of the lower part has a shape symmetric about a longitudinal plane and about a transverse plane, and comprises a third central zone of discontinuity characterized by having a continuous concavity or recess in the lower projection;

said continuous recess is of uniform depth so that its bottom is a spherical surface with radius $r_{i2}$, which is concentric with the spherical surface with radius $r_{i1}$ of the lower projection, said recess being symmetric about said longitudinal and transverse planes, the periphery of the recess being formed by two symmetric and opposed circle arcs with radius $r_{i3}$, a minimum separation Li between said two arcs occurring at the intersection of lower projection by the longitudinal plane, a transition surface from the spherical surface with radius $r_{i1}$ of the lower projection to the spherical surface with radius $r_{i2}$ of the bottom of continuous recess being provided by a wall that is not perpendicular to both said spherical surfaces at each point of periphery of the continuous recess but instead it shows a constant angle of inclination $\phi_i$ with each of said spherical surfaces at each point on the periphery of the continuous recess;

wherein said upper recess of said upper part has a shape symmetric about a longitudinal plane and about a transverse plane, and comprises a fourth central zone of discontinuity characterized by having a continuous shoulder on the upper recess;

said shoulder is of uniform height so that its inward-most part is a spherical surface with radius $rs_2$ which is concentric with the spherical surface with radius $rs_1$ of the upper recess, said shoulder being symmetric about said longitudinal and transverse planes, the periphery of said shoulder being formed by two symmetric opposed arcs with radius $rs_3$, whose minimum separation Ls occurs at the intersection of the upper recess by said longitudinal plane, Ls being greater than the minimum separation Li in the lower projection, a transitional area from the spherical surface with radius $rs_1$ of the upper recess to the spherical surface with radius $rs_2$ of the inward-most area of shoulder is provided by a wall that is not perpendicular to both said spherical surfaces at each point on the periphery of shoulder but instead it shows a constant angle of inclination $\phi_s$ with each of said spherical surfaces at each point on the periphery of the shoulder, said angle $\phi_s$ being smaller than $\phi_i$ and keeping a constant ratio with it;

and wherein ratio $r_{s1}/r_{s2}$ is from 1.10 to 1.20 ratio $r_{i2}/r_{i1}$ is from 1.10 to 1.20 ratio $L_s/L_i$ is from 1.15 to 1.25 ratio $r_{s3}/r_{i3}$ is from 1.05 to 1.10 ratio $\phi_s/\phi_i$ is from 0.75 to 0.90, so that the disc prosthesis is suitable for a cervical spine of a patient.

\* \* \* \* \*